United States Patent [19]

Heber et al.

[11] 4,442,213
[45] Apr. 10, 1984

[54] PROCESS FOR THE PREPARATION OF PLASMINOGEN AND PLASMINOGEN THUS PREPARED

[75] Inventors: Helmut Heber; Horst Schwinn; Norbert Heimburger, all of Marburg; Gerhardt Kumpe, Wetter; Manfred Schick, Marburg, all of Fed. Rep. of Germany

[73] Assignee: Behringwerke Aktiengesellschaft, Marburg, Fed. Rep. of Germany

[21] Appl. No.: 377,312

[22] Filed: May 12, 1982

[30] Foreign Application Priority Data

May 14, 1981 [DE] Fed. Rep. of Germany ....... 3119157

[51] Int. Cl.³ .......................... C12N 9/68; C12N 9/96
[52] U.S. Cl. ................................ 435/217; 435/188
[58] Field of Search .............................. 435/188, 217

[56] References Cited

U.S. PATENT DOCUMENTS 4,361,653  11/1982  Watanabe et al. .................. 435/188

Primary Examiner—Lionel M. Shapiro
Attorney, Agent, or Firm—Curtis, Morris & Safford

[57] ABSTRACT

What is disclosed is a process for rendering plasminogen virtually free of hepatitis virus by heating a plasminogen solution in the presence of a proteinase inhibitor with plasmin specificity, an amino acid, and a saccharide or sugar alcohol.

7 Claims, No Drawings

PROCESS FOR THE PREPARATION OF PLASMINOGEN AND PLASMINOGEN THUS PREPARED

The invention relates to a process for the preparation of human plasminogen which is virtually free of hepatitis virus, by heating plasminogen in the presence of a plasmin inhibitor, preferably aprotinin (basic polypeptide with polyvalent inhibitory activity for proteinases) or soya bean trypsin inhibitor (SBTI), and plasminogen thus prepared.

Blood coagulation and fibrinolysis is a complex process with a stepwise course, which is brought about by a number of physiological and pathological causes, and the course of which depends on about 20 accelerating and inhibiting factors. Disturbances of blood coagulation occur as a result of decreases or increases in the factors affecting blood coagulation and fibrinolysis and these disturbances sometimes manifest themselves as illnesses. Plasminogen is one of these factors.

Preparations containing plasminogen for the alleviation of disturbances which are caused by a deficiency of this protein are known.

However, these are not free of the risk of transmission of hepatitis.

Albumin is regarded to be "hepatitis-safe", that is to say free of the risk of transmission of heptatitis, and thus free of hepatitis viruses capable of multiplication, when it is heated to 60° in an aqueous solution and in the presence of stabilizers (Gellis, S.S. et al., J. Clin. Invest. (1948) 27, 239).

Thus it may be assumed that plasminogen heated in the presence of suitable stabilizers in aqueous solution is equally hepatitis-safe.

A process for stabilizing plasminogen towards heat in aqueous solution by the addition of an aminoacid and a mono- or oligosaccharide or sugar alcohol is described in German Offenlegungsschrift No. 2,916,711; but this process is only satisfactory for solutions containing up to 20 CTA units of plasminogen per milliliter.

Thus the object was to find a process for stabilizing more concentrated aqueous solutions of plasminogen towards heat.

Surprisingly, it has now been found that an aqueous solution of plasminogen can be stabilized towards heat by addition of a proteinase inhibitor, particularly one with specificity for plasmin.

The invention thus relates to a process for the preparation of plasminogen which is virtually free of hepatitis virus, by heating an aqueous solution of plasminogen, which optionally contains an aminoacid and/or a saccharide or a sugar alcohol, wherein the solution contains a proteinase inhibitor.

Examples of suitable proteinase inhibitors are aprotinin or SBTI.

The proteinase inhibitor is added in an amount such that its concentration in the solution is 0.1 to 12.5 APU/ml or 5 to 500 KIU/ml, preferably 0.76 to 2 APU/ml or 30 to 80 KIU/ml (APU=antiplasmin units; KIU=kallikrein inhibition units).

The aqueous solution of plasminogen can be heated in the presence of aprotinin or SBTI until it is virtually certain, by the present state of knowledge, that no hepatitis pathogens will be transmitted, that is to say the plasminogen contains no hepatitis viruses capable of multiplication.

A preparation which is maintained at about 60° C. in aqueous solution for at least 10 hours is regarded nowadays as virtually hepatitis-safe.

A particularly preferred embodiment of the invention comprises treating a solution containing plasminogen prepared, for example, in accordance with German Offenlungsschrift No. 2,057,401, preferably a plasma or placenta fraction, with 0.1 to 12.5 APU of aprotinin or SBTI per ml, preferably 0.75 to 2 APU/ml, (5–500 KIU/ml, preferably 30–80 KIU/ml), and optionally with 1.0 to 3.0 mole/l of at least one of the aminoacids comprising glycine, α- or β-alanine, lysine, arginine, histidine, hydroxyproline, proline, glutamine, an aminobutyric acid, preferably glycine, and 20 to 60% w/w of a mono- or oligosaccharide or sugar alcohol, preferably 1 to 3 mole/l of glycine and 20 to 60% w/w of sucrose and heating to a temperature between 30° and 100° C., preferably 60° to 100° C., and maintaining at this temperature for 1 minute to 48 hours, preferably about 10 hours, the shortest time being associated with the highest temperature and vice versa. The pH should be maintained between the limits 5 and 9, preferably at 6.5.

A preparation of plasminogen is obtained which is virtually hepatitis-safe.

Depending on the solubility of the aminoacid or of the carbohydrate, the concentration can be increased to more than 3 mole/l or 60% by weight respectively, if these components have an appropriately greater solubility at the desired temperature. The heat treatment can also be carried out in several steps.

With the combination of aprotinin with glycine and sucrose, which is preferably used, a hepatitis-safe plasminogen preparation is obtained by heating under the following conditions: 10 to 20 hours heating to 60° to 70° C. of the plasminogen solution, which contains 0.75 to 2 APU/ml (30 to 80 KIU/ml) of aprotinin, 20 to 60% by weight of sucrose and 1 to 3 mole/l of glycine, at a pH of 6 to 7.

As the table shows, the plasminogen in solution is stabilized towards the action of heat (10 hours, 60° C.) by means of aprotinin:

| Stabilizers | Plasminogen (U/ml) | |
| --- | --- | --- |
| | before heating | after heating |
| Sucrose 60% w/w<br>Glycine 2 mole/l | 70 CTA*/ml | 8 CTA/ml |
| Aprotinin 50 KIU/ml<br>Sucrose 60% w/w<br>Glycine 2 mole/l | 70 CTA/ml | 67 CTA/ml |

*CTA Units: Committee on Thrombolytic Agents A. J. Johnson, D. L. Kline, N. Alkjaersig Thromb. Diath. Haemorrh. 21, 259 (1969)

The plasminogen from the heated solution can be purified by adsorption on lysine-MPT adsorbents, washing and eluting, in accordance with German Offenlegungsschrift No. 2,057,401, by which means excess aprotinin is separated off.

It is advantageous to aim at fractions in which plasminogen is enriched, as described, for example, in German Offenlegungsschrift No. 2,057,401.

Monitoring the procedures for enriching and purifying plasminogen is familiar to an expert due to his knowledge of methods of determination of plasminogen. Using these monitoring methods, the process conditions can be controlled from the viewpoint of a satisfactory yield and a satisfactory purity of the product.

Plasminogen can, for example, be determined by the process described by Jacobi et al. in Die Medizinische Welt "26", 1696 (1975).

In order to kill the hepatitis viruses, aprotinin and glycine and sucrose are added to the plasminogen solution and this is heated. For further purification, the heated solution is optionally centrifuged. The supernatant is adsorbed on lysine-MPT adsorbent, the loaded adsorbent is washed and eluted with buffer containing lysine. The invention particularly relates to a hepatitis-safe plasminogen preparation obtainable by this process. In order to increase the storage stability, it is advantageous to add protein-stabilizing substances to the preparation, for example proteins, aminoacids, or carbohydrates. Finally, the preparation subjected to this treatment can be made available in freeze-dried form, the addition of gelatin hydrolysates, for example Haemaccel (R), possibly being advantageous.

The product according to the invention is an agent for the therapeutic substitution of plasminogen in patients in whom plasminogen deficiency is detectable. In additiion, the product can be used for the preparation of a plasminogen-streptokinase complex for thrombolytic therapy.

The invention is illustrated in more detail by the following examples:

EXAMPLE 1

Preparation of a hepatitis-safe plasminogen concentrate from human citrate plasma:

0.5 l of human plasminogen solution containing 110 CTA units of plasminogen/ml were treated with 3 ml of aprotinin solution containing 10 KIU/ml. Then 0.5 kg of sucrose and 75 g of glycine were added and the solution was heated at 60° C. for 10 hours.

EXAMPLE 2

1 l of plasminogen concentrate containing 90 CTA units of plasminogen per ml were tested with 5 ml of aprotinin solution containing 10 KIU/ml. Then 1 kg of sucrose and 150 g of glycine were dissolved therein and the solution was heated at 60° C. for 10 hours.

What is claimed is:

1. A process for preparing plasminogen which is virtually free of hepatitis virus, which comprises heating a solution of plasminogen having a plasminogen concentration greater than 20 CTA units per milliliter which contains a proteinase inhibitor with plasmin specificity, an amino acid, and a saccharide or sugar alcohol.

2. A process as in claim 1 wherein said proteinase inhibitor is aprotinin.

3. A process as in claim 2 wherein said aprotinin is present at a concentration of 0.1 to 12.5 APU/ml (5–500 KIU/ml) of plasminogen solution.

4. A process as in claim 1 wherein said amino acid is glycine, alpha- or beta-alanine, lysine, arginine, histidine, hydroxyproline, proline, glutamine, or an aminobutyric acid and is present at a concentration of 1 to 3 mole/liter of plasminogen solution.

5. A process as in claim 1 wherein said saccharide or sugar alcohol is present at a concentration of 20 to 60 percent (w/w).

6. A process as in claim 1 wherein said plasminogen solution is heated at a temperature from 30° C. to 100° C. for 1 minute to 48 hours.

7. A process for preparing plasminogen which is virtually free of hepatitis virus, which comprises heating a solution of plasminogen having a plasminogen concentration greater than 20 CTA units per milliliter at a temperature of 30° C. to 100° C. for 1 minute to 48 hours, said solution containing 0.1 to 12.5 APU/ml (5–500 KIU/ml) of aprotinin, 1 to 3 mole/liter of glycine, alpha- or beta-alanine, lysine, arginine, histidine, hydroxyproline, proline, glutamine, or an aminobutyric acid, and 20 to 60 percent (w/w) of a saccharide or sugar alcohol.

* * * * *